US005756107A

United States Patent [19]
Hahn et al.

[11] Patent Number: 5,756,107
[45] Date of Patent: May 26, 1998

[54] FORMULATIONS AND METHODS FOR REDUCING SKIN IRRITATION

[75] Inventors: Gary Scott Hahn, Cardiff by the Sea; David Orel Thueson, Poway, both of Calif.

[73] Assignee: Cosmederm Technologies, La Jolla, Calif.

[21] Appl. No.: 362,055

[22] Filed: Dec. 21, 1994

[51] Int. Cl.$^6$ .................................. A61K 7/00; A61K 7/06
[52] U.S. Cl. .............................. 424/401; 424/59; 424/65; 424/70.1; 424/73; 424/195.1; 424/677; 424/722; 424/436; 424/430; 424/49; 424/402; 424/447; 514/846; 514/847; 514/848; 514/859
[58] Field of Search .................................. 424/401, 59, 65, 424/70.1, 73, 195.1, 722, 677; 514/846–848, 859–865

[56] References Cited

U.S. PATENT DOCUMENTS

| | | | |
|---|---|---|---|
| 4,105,782 | 8/1978 | Yu et al. | 424/283 |
| 4,105,783 | 8/1978 | Yu et al. | 424/283 |
| 4,191,750 | 3/1980 | Hodosh | 424/127 |
| 4,285,973 | 8/1981 | Edwards | 424/358 |
| 4,388,301 | 6/1983 | Klein | 424/154 |
| 4,447,439 | 5/1984 | D'Alelio | 424/162 |
| 4,943,432 | 7/1990 | Biener | 424/647 |
| 4,971,800 | 11/1990 | Chess et al. | 424/447 |
| 5,079,010 | 1/1992 | Natterer | 424/617 |
| 5,262,153 | 11/1993 | Mishima et al. | 424/62 |

FOREIGN PATENT DOCUMENTS

| | | |
|---|---|---|
| 085579 | 8/1983 | European Pat. Off. |
| 132126 | 1/1985 | European Pat. Off. |
| 432700 | 6/1987 | European Pat. Off. |
| 484112 | 5/1992 | European Pat. Off. |

OTHER PUBLICATIONS

Abel, Elizabeth A., "Phototherapy", *Dermatologic Clinics*, 13(4):841–849, Oct. 1995.
Arky, Ronald, et al. (Eds.), *Physicians Desk Reference*, 49th Edition, 1995, p. 929.
Bayless, J. Mark, et al., "Diagnosis and Treatment of Acute Fluoride Toxicity", *Am. Dental Ass'n.*, 110:209–211, Feb. 1985.
Bilotto, Gerardo, et al., "Effects of Ionic and Non–Ionic Solutions on Intradental Nerve Activity in the Cat," *Pain*, 32: 231–238, 1988.
Budavari, Susan, et al. (Eds.), *The Merck Index*, (Merck & Co., Inc., 1989), pp. 708, 1218.
Degroot, *Unwanted Effects of Cosmetics and Drugs Used in Dermatology*, 1995, p. 229.
*Drug Facts and Comparisons*, 1995 Edition (Facts and Comparisons, St. Louis, MO), pp. 37–38.
Fitzpatrick, Thomas B., et al. (Eds.), *Dermatology In General Medicine*, (McGraw–Hill, Inc. 1993), 4th Ed., vol. 1, pp. 501, 508–510.
Gilman, Alfred Goodman et al., *The Pharmacological Basis of Therapeutics*, (McGraw–Hill, Inc. 1993), pp. 1291, 1581, 1586.
Gonzalez, Ernesto, "PUVA for Psoriasis", *Dermatologic Clinics*, 13(4):851–866, Oct. 1995.
Greaves, Malcolm W., et al., "Treatment of Psoriasis," *New Engl. J. Med.*, 332(9): 581–588, Mar. 1995.

(List continued on next page.)

*Primary Examiner*—Sallie M. Gardner
*Attorney, Agent, or Firm*—Lyon & Lyon LLP

[57] ABSTRACT

Topical formulations comprising an anti-irritant amount of aqueous-soluble lithium ($Li^+$) or potassium ($K^+$) cation, and methods for using the same to inhibit skin irritation, are disclosed.

54 Claims, 5 Drawing Sheets

OTHER PUBLICATIONS

Griffiths, Tamara W. et al., "Immunopathogenesis and Immunotherapy of Psoriasis", *Dermatologic Clinics*, 13(4):739–749, Oct. 1995.

Hallmans, Goran, "Local Absorption of Zinc from Wounds Treated with Different Concentrations of Zinc Sulphate", *Acta Dermatovener (Stockholm)*, 58:413–419, 1978.

Jeffes III, Edward W.B., et al., "Methotrexate and Other Chemotherapeutic Agents Use to Treat Psoriasis", *Dermatologic Clinics*, 13(4): 875–890, Oct. 1995.

Katz, H. Irving, "Topical Corticosteroids", *Dermatologic Clinics*, 13(4):805–815, Oct. 1995.

Kim, Syngcuk, "Hypersensitive Teeth: Desensitization of Pulpal Sensory Nerves," *J. Endodontics*, 12(10): 482–485, Oct. 1986.

Koo, John et al., "Cyclosporine: What Clinicians Need to Know", *Dermatologic Clinics*, 13(4):897–907, Oct. 1995.

Kragballe, Knud, "Vitamin $D_3$ Analogues", *Dermatologic Clinics*, 13(4):835–839, Oct. 1995.

Lansdown, A.B.G., "Interspecies Variations in Response to Topical Application of Selected Zinc Compounds", *Food Chem. Toxic.*, 29(1):57–64, 1991.

Lebwohl, Mark, "Future Psoriasis Therapy", *Dermatologic Clinics*, 13(4):915–923, Oct. 1995.

Lowe, Nicholas J., et al., "Generalized Pustular Psoriasis Precipitated by Lithium Carbonate," *Arch. Dermatol.*, 114: 1788–1789, Dec. 1978.

Markowitz, K., et al., "Decreasing Intradental Nerve Activity in the Cat with Potassium and Divalent Cations," *Archs. Oral Biol.*, 36(1): 1–7, 1991.

Markowitz, Kenneth, et al., "The Role of Selected Cations in the Desensitization of Intradental Nerves," *Proc. Finn. Dent. Soc.*, 88 (Suppl I): 39–54, 1992.

Momtaz-T., Khosrow, "Modifications of PUVA", *Dermatologic Clinics*, 13(4):867–873, Oct. 1995.

Morris, Christopher J. et al., "Reactive Oxygen Species and Iron—a Dangerous Partnership in Inflammation", *Int. J. Biochem. Cell Biol.*, 27(2):109–122, 1995.

Salvato, Anthony R., et al., "Clinical Effectiveness of a Dentrifice Containing Potassium Chloride as a Desensitizing Agent," *Am. J. Dent.*, 5(6): 303–306, Dec. 1992.

Serup, Jorgen et al., "Epidermal Hydration of Psoriasis Plaques and the Relation to Scaling: *Measurement of Electrical Conductance and Transepidermal Water Loss*", *Acta Derm Venereol (Stockholm)*, 67:357–359, 1987.

Silverman, A.K., et al., "Tars and Anthralins," *Dermatologic Clinics*, 13(4): 816–834, Oct. 1995.

Tagami, Hachiro et al., "Interrelationship Between Water-Barrier and Reservoir Functions of Pathologic Stratum Corneum", *Arch. Dermatol.*, 121:642–645, May 1985.

Wieder, Joshua M. et al., "Systemic Retinoids for Psoriasis", *Dermatologic Clinics*, 13(4):891–896, Oct. 1995.

Wilkinson, J.B., et al. (Eds.), *Harry's Cosmeticology* (Chemical Publishing Company, New York, New York, 1982), p. 74.

FORMULATIONS AND METHODS FOR REDUCING SKIN IRRITATION

BACKGROUND

Many substances are applied topically to the skin or mucous membranes of humans or animals in order to alter the subject's appearance, to protect the subject from the environment, or to produce a biological change in the skin or other tissue for therapeutic, preventive or cosmetic purposes. These substances may generically be termed "topical products" and include such topically applied substances as cosmetics, over-the-counter and prescription topical drugs, and a variety of other products such as soaps and detergents.

Topical products occur in a variety of forms, including solids, liquids, suspensions, semisolids (such as creams, gels, pastes or "sticks"), powders or finely dispersed liquids such as sprays or mists. Examples of topical products commonly classified as "cosmetics" include skin care products such as creams, lotions, moisturizers and "treatment cosmetics" such as exfolients and/or skin cell renewal agents; fragrances such as perfumes and colognes, and deodorants; shaving-related products such as creams, "bracers" and aftershaves; depilatories and other hair removal products; skin cleansers, toners and astringents; pre-moistened wipes and washcloths; tanning lotions and sunscreens; bath products such as oils; eye care products such as eye lotions and makeup removers; foot care products such as powders and sprays; skin colorant and make-up products such as foundations, blushes, rouges, eye shadows and liners, lip colors and mascaras; lip balms and sticks; hair care and treatment products such as shampoos, conditioners, colorants, dyes, bleaches, straighteners, and permanent wave products; baby products such as baby lotions, oils, shampoos, powders and wet wipes; feminine hygiene products such as deodorants and douches; skin or facial peels applied by dermatologists or cosmeticians; and others. Examples of topical products commonly classified as "topical drugs" are many and varied, and include over-the-counter and/or prescription products such as antiperspirants, insect repellents, sunscreens and sunburn treatments, anti-acne agents, antibiotics, therapeutic retinoids, anti-dandruff agents, external analgesics such as capsaicin products, topical contraceptives, topical drug delivery systems, suppositories and enemas, hemorrhoid treatments, vaginal treatments, lozenges, and many other products with therapeutic or other effects. Other topical products include hand, facial and body soaps and detergents and other forms of skin cleansers, as well as household detergents and many other household products such as solvents, propellants, polishes, lubricants, adhesives, waxes and others which are either applied topically or are topically exposed to the body during normal use.

In a large number of cases, topical products contain chemicals which may produce irritation or inflammation when applied to the skin (including the mucosa). The present invention is directed in part to compositions and methods for inhibiting the irritation associated with such topical products.

The occurrence, frequency and nature of topical-product-induced irritation often varies from user to user. The severity of irritation to the susceptible user may range from subclinical to mild to severe. Typical symptoms of irritation include itching (pruritus), stinging, burning, tingling, "tightness," erythema (redness) or edema (swelling). The irritation response may be due to the direct effect on the skin of certain topical product chemicals or to a response by the immune system directed toward the chemicals alone or in combination with skin components (e.g. allergic dermatitis).

The sensation of itch is one of the most common skin problems experienced by humans and animals. Itch can be defined as a sensation which provokes the desire to scratch the site from which the sensation originates. All skin contains sensory nerves which transmit itch in response to chemical irritation, environmental exposure or disease processes. Although the precise population of itch producing nerves have not been identified, the thinnest, unmyelinated nerve population, termed type C nociceptive neurons are thought to be the most important in producing the sensation. Itch: Mechanisms and Management of Pruritus, Jeffrey D. Bernhard, McGraw-Hill, Inc. (San Francisco, 1994), pp. 1–22. The itch-producing nerves of the skin can be considered to be a "final common pathway" for the many irritating conditions which are ultimately sensed as itch including chemical exposure, environmental exposure (such as that which produces dry, itchy skin) and disease processes such as atopic dermatitis. Many chemical substances are able to produce itch when topically applied to the skin. No matter what the ultimate cause of itch, the sensation experienced is the same and provokes the desire to scratch.

Many ingredients used in topical products are known irritants or are potentially irritating, especially to people with "sensitive skin". These irritating ingredients include fragrances, preservatives, solvents, propellants and many other ingredients that might otherwise be considered inert components of the products. Additionally, many topical product active ingredients, including chemicals that may also be classified as drugs, produce irritation when applied to the skin. These include, but are not limited to, such ingredients as exfoliants and skin cell renewal agents, anti-acne drugs, antiperspirant compounds, antihistamines, anti-inflammatory agents, skin protective agents, insect repellent chemicals, sunscreens and many others. Where more than one chemical irritant is present, their irritating effects may be additive. Furthermore, chemical ingredients may react with one another, or in the environment of the skin, to form new chemicals which are irritating. The vehicles in which the active drug ingredients are formulated may also produce irritation in sensitive people, especially in drugs such as topical corticosteroids.

In addition to chemicals which directly trigger skin irritation, some chemicals indirectly cause the skin to become more sensitive to other chemicals or environmental conditions which would not normally cause irritation. Many chemicals which act as skin "exfoliants" such as retinoids (e.g. tretinoin, retinol and retinal), carboxylic acids including α-hydroxy acids (e.g. lactic acid, glycolic acid), β-hydroxy acids (e.g. salicylic acid), α-keto acids, acetic acid and trichloroacetic acid, 1-pyrrolidone-5-carboxylic acid, capryloyl salicylic acid, α-hydroxy decanoic acid, α-hydroxy octanoic acid, gluconolactone, methoxypropyl gluconamide, oxalic acid, malic acid, tartaric acid, mandelic acid, benzylic acid, gluconic acid, benzoyl peroxide and phenol, among others, may cause the skin to become more sensitive to irritation triggered by other topically-applied chemicals such as moisturizers, sunscreens, fragrances, preservatives, surfactants (e.g. soaps, shaving cream) and other topical products. Exfoliants and other ingredients may also increase the skin's sensitivity to environmental conditions such as sunlight, wind, cold temperature and dry air, or may exacerbate the irritation attributable to a pre-existing skin disease.

Conversely, environmental influences may themselves increase the skin's sensitivity to chemicals in topical products by reducing the skin's "barrier function." The barrier function acts to minimize absorption or passage of potentially irritating chemicals through the outer "dead" cell layer into the living skin tissue. Extremes of humidity, for example, can greatly increase irritation from topically-applied products. A very common condition due to low humidity is termed "winter itch" in which the very low humidity characteristics of many cold climates (particularly when accompanied by indoor heating) or long exposure to refrigerated air from air conditioners in the summer produces itchy skin—especially in older people—which can exacerbate the irritating effects of topical products. Additionally, soaps, detergents, cleansing products, shaving creams, alcohol and other products which remove some of the skin's protective lipids and/or secretions may increase the skin's permeability and sensitivity to topically-applied chemicals which would otherwise not produce irritation. Normal processes such as sweating may also increase the ability of irritant materials, such as antiperspirants, deodorants or sunscreens, to penetrate the skin through pores or glands, thus exacerbating the potential for irritation. Exposure of the skin to high humidity environments or liquids may also increase the ability of potential irritants to penetrate the skin. Similarly, the skin may become sensitized or inflamed due to infection, shaving abrasion, repeated or excessive washing or bathing, sun exposure, or other mechanical abrasion or injury, resulting in sensory irritation responses upon subsequent application of underarm deodorants, after-shaves or other topical products.

In addition to chemical and environmental causes of skin irritation, many people have an inherent sensitivity or genetic predisposition to skin irritants. People with respiratory allergies, for example, tend to have excessively dry skin which facilitates increased absorption of potentially irritating chemicals. The excessively dry skin which accompanies atopic dermatitis, for example, predisposes patients with this condition to irritation from many topically-applied products. Other skin diseases and conditions such as allergic or non-allergic contact dermatitis, psoriasis, eczema, candida albicans, post-herpetic neuralgia, infectious diseases manifested by, for example, sore throat or skin lesions, insect bites and the like produce inherent irritation which may be exacerbated by application of topical products. Many other individuals exhibit sensitive skin as a condition that is not related to an identifiable skin disease.

Whatever the exact cause of irritation, many attempts have been made to reduce the irritation potential of topical products by identifying chemicals which tend to cause irritation and reducing their concentration or eliminating them from the products. Many of these products are advertised to consumers as "hypoallergenic" or the like to, designate a product's reduced tendency to cause irritation in consumers with sensitive skin. Most skin or mucosal irritation responses, however, are not allergic in origin. In any event, it is often not feasible or practical to identify or eliminate all of the irritating chemical(s), particularly when the irritating chemical(s) are the active ingredient of the product or are required for formulation, preservative or other functional reasons.

As one example, there is a substantial practical and commercial need in the field of exfolients and related skin care products for a composition or method that will reduce or prevent the irritation caused by such products. Common exfolients include α- and β-hydroxy carboxylic acids such as lactic acid, glycolic acid, salicylic acid and the like, α-keto acids such as pyruvic acid, as well as assorted compounds such as acetic acid and trichloroacetic acid, 1-pyrrolidone-5-carboxylic acid, capryloyl salicylic acid, α-hydroxy decanoic acid, α-hydroxy octanoic acid, gluconolactone, methoxypropyl gluconamide, oxalic acid, malic acid, tartaric acid, mandelic acid, benzylic acid, gluconic acid, peroxides, phenols, and skin cell renewal agents such as retinoids. Such products are used as exfoliants and/or cell renewal agents to reduce the occurrence or severity of skin wrinkles, particularly facial wrinkles, or as anti-acne, anti-"dry skin" or skin whitening agents. See U.S. Pat. Nos. 4,105,782, 4,105,783, 4,246,261, and 5,091,171 (Yu et al.) and 5,262,153 (Mishima et al.); W. P. Smith, "Hydroxy Acids and Skin Aging," Soap/Cosmetics/Chemical Specialties for September 1993, p. 54 (1993). Hydroxy acids, in concentrations high enough to exfoliate, are well known often to cause skin irritation and rashes. The danger of irritation is even higher for persons that have sensitive skin.

Currently available methods reported by Yu et al. to reduce the irritation caused by hydroxy- and keto-acids in topical products include adding a strong alkali metal base such as sodium hydroxide or potassium hydroxide, thereby raising the pH of the preparation and reducing the acidity of the hydroxy acid. Such methods have the reported drawback of reducing the ability of the resulting hydroxy acid salt to penetrate the skin and thus compromising the beneficial effects (particularly anti-acne or anti-"dry skin" effects) of the hydroxy acid. Alternatively, Yu et al. have proposed the approach of formulating the hydroxy acid with a non-alkali metal base such as ammonium hydroxide or an organic base such as a primary, secondary or tertiary organic amine, thereby forming an amide or ammonium salt of the active ingredient hydroxy (or keto) acid. See U.S. Pat. Nos. 4,105, 782 and 4,105,783 (Yu et al.). The effect of such formulations is, again, to raise the pH of preparation to a non-irritating level. However, the increased pH (reduced acidity) of the resulting preparations renders them less efficacious as exfoliating or anti-wrinkle agents, which desirably have an acidity equivalent to pH 1–6, and more preferably pH 3–5. See Smith, above, at Table 1. Other approaches to reducing the irritation associated with exfolient products include the use of slow-release topical formulations such as polymer-based vehicles (see, e.g., Chess et al., U.S. Pat. No. 4,971, 800) or microsponges, and inclusion of, e.g., plant-derived anti-irritant components (see, e.g., Smith et al., U.S. Pat. No. 5,028,428).

Mishima, et al. have reported that certain alkali or alkaline-earth metal salts of lactic acid were useful as skin-whitening agents (U.S. Pat. No. 5,262,153), but no recognition is expressed as to any need or ability to reduce irritation effects; in addition, the particular formulations of Mishima were typically "neutralized" or adjusted to pH 5.5 prior to screening or skin-whitening testing (see Experiments 1 and 2). A clear need exists, therefore, for a composition or method that prevents or reduces the skin irritation caused by low-pH (high-acidity) organic or inorganic acid products but that does not reduce the efficacy of the acids as exfoliant/cell-renewal agents.

More generally, it would be highly desirable to identify compounds with anti-irritant activities that would reduce the irritation caused by a wide range of otherwise safe and effective topical products, or to reduce the intrinsic irritation associated with various skin diseases and conditions (such as atopic dermatitis, eczema or psoriasis) or caused by exposure to irritating chemicals or environmental conditions such as sun, wind or extremes in humidity.

As explained in more detail below in the Detailed Description, the present invention involves the surprising discovery that the metal cations of the invention are useful in reducing the incidence and severity of irritation associated with topically applied skin irritants. While the exact mechanism (or mechanisms) of activity of such cations is not known and the invention is not limited to any particular mechanism, it is presently believed that the cations of the invention may reduce irritation by interacting with epidermal nerve cells to prevent or counteract the sensation of irritation, and/or by interfering with irritation-inducing components of skin cells that are triggered by the application of the skin irritant. Thus, the cations may alter the ability of epidermal nerve cells to depolarize or repolarize, as for example by blocking or interfering with ion channel or pump operation or by altering the transmembranal action potential, or the cations may interfere with the transmission of nerve impulses from one nerve cell to another (as by suppressing neurotransmitter release). General descriptions of the function of channel proteins are given in B. Hille (ed.), *Ionic Channels of Excitable Membranes*, Sinauer Associates (Sunderland, Mass.: 2d Ed. 1992), and Siemen & Hescheler (eds.), *Nonselective Cation Channels: Pharmacology, Physiology and Biophysics*, Birkhauser Velgag (Basel, Switzerland: 1993). In addition, or alternatively, the cations of the invention may act to inhibit or modify the action of skin cell proteases or other irritation-inducing biological molecules (such as eicosanoids or cytokines) that may otherwise be activated by topical application of skin irritants, or may alter "second-messenger" function within sensory cells.

A number of ionic species, and certain metal cations in particular, have been associated with various aspects of nerve cell activity. For example, during the resting (polarized) state of a typical nerve cell, the intracellular concentration of potassium in the nerve axon is high relative to the extracellular potassium concentration, and the intracellular concentration of sodium is low relative to the extracellular sodium concentration. During the process of nerve depolarization, potassium ions flow out of the cell across the membrane, and sodium ions flow into the cell, through pores created by axonal membrane proteins known as "channels". Following depolarization, membranal proteins known as ion "pumps" act to reestablish the resting, polarized state of the cell.

A number of cationic species, including the potassium ion itself ($K^+$), are known to interact with potassium channels so as to mediate potassium fluxes or to block or otherwise modulate the action of such channels. Smith & Reynard (eds.), *Textbook of Pharmacology* W. B. Saunders (Philadelphia: 1992), p. 81; B. Hille (ed.), *Ionic Channels of Excitable Membranes*, Sinauer Associates (Sunderland, Mass.: 1992), pp. 130–31; Spielman et al., "The Diversity of Bitter Taste Signal Transduction Mechanisms," in *Sensory Transduction* (Corey & Roper, eds.), Rockefeller University Press (New York: 1992), pp. 310–313. Potassium nitrate, also known as saltpeter, has historic use as a diuretic, although it is not used for that purpose in most countries today. With the exception of its use in toothpastes for people with painful, sensitive teeth, potassium nitrate appears not to be currently used for any significant therapeutic purposes in the United States (see *Physicians' Desk Reference*, Medical Economics Data Production Co. (Montvale N.J.: 1995); *Physicians' Desk Reference for Nonprescription Drugs*, Medical Economics Data Production Co. (Montvale N.J.: 1994)).

Lithium cation (which, like potassium, is monovalent), is used as a treatment for manic-depressive (bipolar) disorders. Lithium has also been reported to block sodium channels on cell membranes. Many common local anesthetics are either tertiary amino esters or amides of aromatic acids having a positively-charged cation portion which is responsible for interruption of impulse conduction. This effect is generally achieved by prevention of migration of sodium ions across the nerve membrane through sodium channels, and perhaps also by competition with calcium ions at reciptor sites which control permeability. M. D. Vickers et al., *Drugs in Anaesthetic Practice* Butterworth-Heinemann Ltd. (Oxford: 7th Ed. 1991), Ch. 6, pp. 200–202; A. G. Gilman et al., *Goodman and Gilman's The Pharmacological Basis of Therapeutics*, McGraw Hill (8th Ed. 1993), pp. 312–313.

While laboratory studies such as these using cultured single cells or microelectrode single-cell electrophysiological techniques have done much to advance the understanding of nerve activity, distinct challenges are presented in the clinical setting. A number of factors make it difficult to predict what effects, if any, particular agents (cationic or otherwise) may have on nerve activity and sensation in intact animal bodies. For example, the animal body (and particularly the human body) contains a wide variety of nerve-containing tissues and organs adapted to perform many different and specialized functions. Other cells in the body—notably muscle cells and neuro-endocrine secretory systems—are "excitable" in a manner akin to nerve cell excitation. In order to achieve the disparate functions required in the animal body, the various tissues and organs are differently disposed within the body, and the nerves (and other excitable cells) within a given tissue are typically highly specialized as well as uniquely disposed within the particular tissue. As a result, different nerve-containing tissues may respond differently to a given agent depending on, for example, the type of nerve (or other excitable) cell and its structural disposition within the tissue, the mode of administration of the agent, the ability of the agent to penetrate to the respective nerve site, and the rate at which the agent is removed from the nerve site.

For example, while certain divalent cations including magnesium and calcium have long been reported in laboratory studies to have a "depressant" effect on nerves, clinical studies have shown that intravenously-administered magnesium sulfate produces neither anesthesia nor even analgesia in humans (Kato et al., Can. Anaes. Soc. J. 15, 539–544 (1968)). Instead, the magnesium ion induces paralysis of skeletal muscles, due perhaps to the inhibitory effects of magnesium on muscle cell activity. Oral ingestion of large doses of magnesium (e.g., magnesium sulfate as a laxative) does not result in paralysis or depressed neural activity in healthy individuals. On the other hand, when magnesium is applied directly to the brains of test animals, depressed neural or synaptic activity, and even a sleep-like state, reportedly result (Kato et al. (1968), above).

In addition, the mechanisms underlying sensory stimulation and perception in the animal body are diverse and exceedingly complex. Even within a single tissue or organ, different nerve groups having different organizations and functions may appear. Depending on how they are disposed within the tissue, the various nerve groups may be differently affected (or affected not at all) by an applied agent. Moreover, to the extent that different types of nerve cells occur within a tissue, they may have different susceptibilities to a particular applied agent. This is particularly true in the skin, which has nerves adapted to sense a wide variety of sensory inputs.

Another complicating factor arises from the detailed nature of nerve cell activity and response. The firing activity of an individual nerve cell may be influenced in a complex fashion, and may vary over time, depending on such factors as the extracellular and intracellular concentration of nerve-related ions as sodium, potassium, chloride, calcium and the like, as well as the time course of exposure to such ions. Other bioactive agents, such as prostaglandins present during inflammatory responses, may further influence nerve sensitivity. In addition, nerves may respond to non-chemical stimuli such as hydrodynamic pressure changes, which in turn may depend on the nature of the tissue in which the nerve is disposed. Such factors lead to considerable clinical uncertainty as to how various agents may affect nervous responses such as pain responses.

For example, studies have been undertaken over the last several decades in an effort to identify and elucidate the effects of various putative tooth-desensitizing agents and therapies. Tooth nerves are disposed primarily in the central pulp of the tooth, but also extend partially into the surrounding "dentin" material. The dentin material is a mineralized collagen matrix containing microscopic, fluid-filled "dentinal tubules." It has long been known that tooth nerve activity (which is sensed as pain) may be triggered by hydrodynamic pressure changes in the tubule fluid, as may be caused for example by probing or air-blasting the tooth or by applying an ionic solution having a high osmotic pressure (particularly when the protective enamel surrounding the dentin is degraded). Accordingly, one reportedly effective treatment for tooth hypersensitivity involves sealing or occluding the dentinal tubules using chemical or physical means (Scherman & Jacobsen, J. Am. Dent. Ass. 123, 57–61 (1992)). In addition, potassium and strontium salts, particularly potassium nitrate and strontium chloride, have been employed in dentifrices and are reported to reduce tooth sensitivity following two to six weeks of continuous use (Scherman & Jacobsen, above; Silverman, Comp. Cont. Dent. Educ. 6, 131–136 (1985)). One mechanism commonly advanced to explain this putative desensitizing activity is that precipitated potassium or strontium ions block or inhibit fluid flow within the dentinal tubules (Scherman & Jacobsen, above; Knight et al., J. Periodontal Res. 64, 366–373 (1993)). This explanation is consistent with the chemical/physical sealing therapies noted above, and also appears consistent with the clinical observation that several weeks of treatment are required in order to achieve substantial desensitizing effects.

A number of studies have attempted to elucidate other possible effects of various ions on tooth nerve activity, and have established that such effects may vary greatly depending on the clinical or experimental system employed. For example, pain is induced when potassium ion is applied to exposed tooth pulp but not when applied to the dentin (Nahri et al., Arch. Oral Biol. 27, 1053–58 (1982). Hypertonic solutions of calcium and magnesium salts have been reported to evoke pain and/or transient nerve electrical activity when applied to the dentin, probably due to dentinal tubule water movement induced by osmotic pressure effects (Orchardson, in Lisney & Matthews (eds.) Current Topics in Oral Biology, University of Bristol Press (Bristol: 1985), pp. 205–215; Nahri, above; Markowitz & Kim, Proc. Finn. Dent. Soc. 88 (Supp. 1), 39–54 (1992)). On the other hand, electrical activity studies undertaken on exposed tooth nerves (obtained, for example, by deeply abrading the dentin material) have indicated that various divalent cations (particularly calcium and magnesium) may suppress nerve electrical responses, while monovalent potassium evokes a transient electrical response followed by inhibition of excitability (Markowitz & Kim, above; Orchardson, above). In the final analysis, the Markowitz and Kim group concluded that it is difficult to explain the clinical desensitizing effects of the available ionic desensitizing dentrifices (which require several weeks of treatment) in terms of a direct nerve cell membrane function, and that studies undertaken with exposed nerves may not reflect the pain-induction mechanisms observed clinically (Markowitz & Kim, above).

The human skin presents a sensory and structural environment that is much more complicated than that of the tooth. For example, the skin contains nerves and highly specific sensory organs that are specialized and disposed so as to differentiate the stimuli leading to such distinct sensations as heat, cold, pressure, pain, itch and the like. In addition to normal sensory stimuli, nerves in the skin are also responsive to native or foreign chemicals such as proteases, prostaglandins, complement-system molecules, allergens, mitogens and the like which may be presented due to tissue injury or environmental exposure. Agents which are effective to combat one source of sensory stimulus—for example steroidal agents to treat skin inflammation—are ineffective against other sensory stimuli such as pressure, heat, or the transitory sting or itch caused by an applied skin care product. Conversely, local anesthetic agents which are effective to depress all sensory or even motor activity in a treated region are not desirable if only a single sensation—for example a transitory sting or itch—is sought to be eliminated. To complicate the situation, the structural matrix of the skin affords a "barrier function" which tends to exclude or inhibit the entry of foreign material, including potentially therapeutic agents.

Accordingly, it would be desirable to identify agents which are effective in the skin to inhibit certain identified sensory responses (as for example pain or itch) while not adversely affecting other nervous responses in the same tissue (as for example tactual sensations).

SUMMARY OF THE INVENTION

The present invention is directed to the use of the monovalent cations potassium ($K^+$) and lithium ($Li^+$) and salts of the foregoing cations as ingredients to provide fast-acting, efficient and safe topical skin anti-irritant effects, and to formulations containing such selected cations. It is one object of the present invention to provide ingredients, formulations and methods of use which can suppress skin irritation due to chemical or environmental exposure, or due to tissue inflammation, injury or other skin pathology. The invention is particularly useful for preventing, reducing or eliminating the potential irritation caused by topical application of products containing other irritating ingredients, including cosmetics such as especially hydroxy acid or other exfolient containing products, facial peels, shaving products, sunscreen products, deodorants and other cosmetics as described above, as well as topical drug products containing irritating active ingredients or vehicles, and other products such as soaps, detergents, solvents and the like which are either applied topically or are topically exposed to the body during use. Thus, the present invention meets a clear need for formulations and ingredients that will prevent or reduce the potential skin irritation caused by topical products. The invention is also useful for preventing, reducing or eliminating the skin irritation caused by skin diseases or other conditions such as environmental exposure to irritating chemicals or influences such as wind, heat, cold and extremes in humidity, including the intrinsic irritation associated with these conditions as well as such irritation as may be exacerbated by the application of a topical product.

Preferred embodiments of the present invention utilize one or more of the identified cations accompanied (as in the form of a salt) by one or more ionizing anionic species, preferably an acidic anion species such as a chloride, nitrate, sulfate, acetate, gluconate or oxalate anion, dissolved or dispersed in an appropriate vehicle. Investigations relating to the present invention have shown that the anti-irritant effects of the cations of the invention can be optimized by suitable selection of the accompanying anionic species. Especially preferred cation-anion pairs include potassium nitrate, potassium chloride, potassium oxalate, and potassium gluconate; and lithium acetate, lithium carbonate, lithium sulfate and lithium nitrate. In the preferred embodiments, the potassium cation of the invention is included in a suitable topical vehicle at a concentration of about 100 to about 3000 mM, more preferably about 400 to about 2000 mM, and most preferably about 700 to about 1500 mM. The lithium cation of the invention is included in a suitable topical vehicle at a concentration of about 10 to about 3000 mM, more preferably about 50 to about 2000 mM, and most preferably about 100 to about 1000 mM. The appropriate cation concentration can be achieved using a single metal cation species of the invention, or multiple different cation species may be combined to yield the total desired cation concentration.

In another preferred embodiment, one or more of the cations of the invention is combined in a topical product formulation further comprising a potentially irritating ingredient, the cation(s) being present in a total amount effective to reduce or eliminate irritation due to the irritant ingredient.

In another preferred embodiment, one or more of the cations of the invention is paired with one or more anionic species selected so as to achieve a desired level of acidity or basicity in the formulated composition, and a total cation concentration effective to reduce skin irritation. In one such particularly preferred embodiment, a cation of the present invention is combined in a hydroxy acid or other exfolient preparation accompanied by one or more suitable anionic species such that the pH of the hydroxy acid preparation is maintained in the range of pH 1–6, and more preferably in the range of pH 3–5. It will be understood that, where the formulation employs an anhydrous vehicle, the acidity of the formulation may not be expressible in typical pH terms, but that such acidity will manifest itself upon exposure of the formulation to the skin where water is present both intracellularly and extracellularly.

In another embodiment, the cations of the present invention may be combined in a formulation with other anti-irritants, such as steroidal or non-steroidal anti-inflammatory agents or other materials such as aloe vera, chamomile, α-bisabolol, Cola nitida extract, green tea extract, tea tree oil, licorice extract, allantoin, urea, caffeine or other xanthines, glycyrrhizic acid and its derivatives, or with other anti-irritant species such as those identified in co-pending patent application Ser. Nos. 08/362,100, 08/362,101, 08/362,097 and 08/362,058 (attorney docket numbers 209/250, 210/181, 210/182, and 210/184, entitled "Formulations and Methods for Reducing Skin Irritation"), filed on Dec. 21, 1994 by the present inventors, so as to achieve a multiple anti-irritant effect.

The invention further provides methods of treating, reducing or eliminating skin irritation comprising the topical application of a formulation comprising an anti-irritant effective amount of one or more cationic species of the invention. The cation formulation may further include one or more potentially irritating components. Alternatively, the cation formulation may be applied separately and prior to application of another product containing a potentially irritating component, or the cation formulation may be applied alone in order to prevent the development of irritation or to treat a pre-existing irritation attributable to conditions such as skin disease, chemical irritant exposure or environmental exposure.

DETAILED DESCRIPTION

Figure 1:
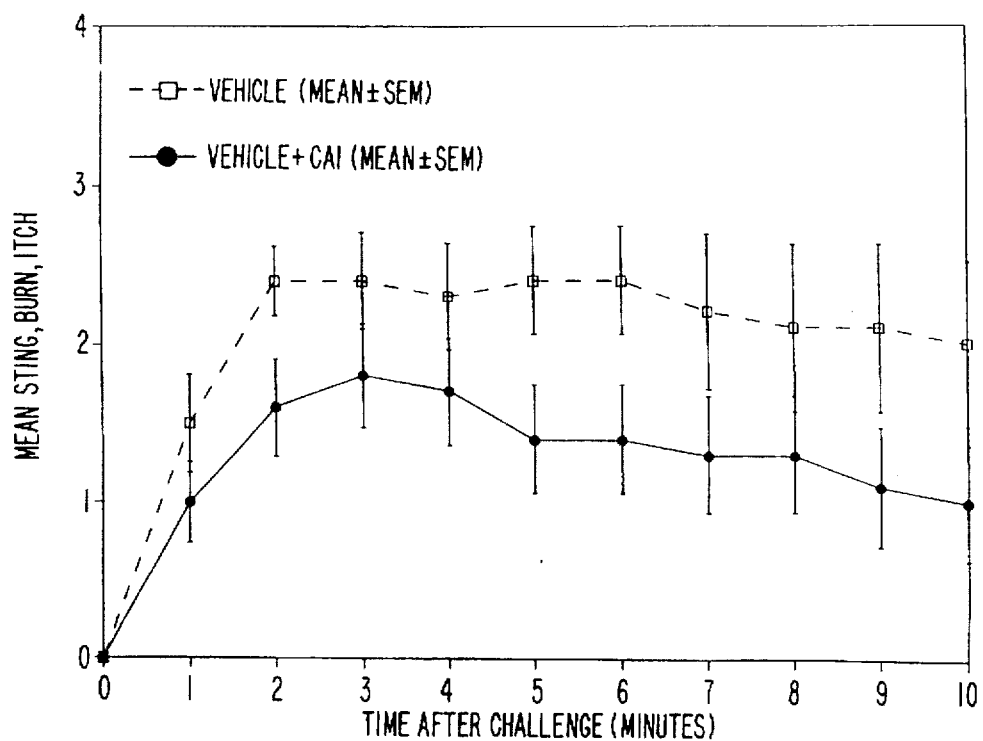
FIGS. 1 through 4 depict experimental data showing the time course of irritation responses (FIG. 1), the cumulative irritation over time (FIG. 2), and the subject-by-subject cumulative irritation suppression and irritation responses (FIGS. 3 and 4) for a panel of humans treated with 250 mM potassium chloride (and control) in a lactic acid skin irritation challenge.

Human clinical trials undertaken in connection with the present invention have established that the cation species potassium ($K^+$) and lithium ($Li^+$) are effective, when applied topically to the skin in appropriate concentrations and vehicles, to suppress the relatively severe stinging, burning, tingling, itching and/or erythema induced by topical application of the hydroxy acid skin irritant lactic acid. Formulations containing such cations are useful in suppressing a wide range of topical-product-induced irritation responses attributable to exfoliants, sunscreens, retinoids, antiperspirants, deodorants, anti-acne and other products which contain components potentially capable of causing sensory irritation. For example, the cations of the present invention are useful for preventing or reducing the skin irritation caused by α- or β-hydroxy acids, α-keto acids and other carboxylic acids, as well as retinoids, phenols, peroxides and similar irritants found in over-the-counter topical products for home or cosmetologist use (such as 1-pyrrolidone-5-carboxylic acid, capryloyl salicylic acid, α-hydroxy decanoic acid, α-hydroxy octanoic acid, gluconolactone, methoxypropyl gluconamide, oxalic acid, malic acid, tartaric acid, mandelic acid, benzylic acid, and gluconic acid), as well as in certain prescription topical drugs containing high (for example, 12% w/w or even higher) dosage forms of such irritants. The irritation attributable to combinations of such irritating ingredients, such as lactic acid/salicylic acid combinations and hydroxy acid/retinoid combinations, as well as irritation attributable to purified isomeric forms of such ingredients, can also be inhibited by the formulations of the invention. Additionally, formulations containing such cations are useful in ameliorating irritation in conditions where the skin is inherently hypersensitive to topical products (e.g. dry skin, "winter itch," and other inflammation or injury conditions) and in ameliorating the irritation due to such conditions even in the absence of other applied topical products. The formulations are also useful in treating non-human animal skin irritation, as for example dog or cat irritation and resultant scratching due to fleas or other skin disease or condition.

An additional benefit of the present anti-irritant compounds and formulations is that they do not have the undesirable anesthetic side-effects exhibited by Lidocaine and other similar skin local anesthetics. Upon application of a solution of the compound used in the clinical trials described here, subjects typically reported no sensations other than those sensations caused by the vehicle alone, and no lack of normal sensation(s).

Formulations of the Invention

The anti-irritant topical formulations of the invention comprise a topical vehicle suitable for administration to the animal (particularly human) skin, and an amount of one or more cations of the invention effective to reduce, inhibit or eliminate existing or potential skin irritation or inflammation. The cations are, of course, accompanied in the formulation by one or more charge-neutralizing anionic counterions, although the cation-anion pairs as originally incorporated into the vehicle may become dissociated in the resulting formulation, or the cations of the invention may become associated in the formulation with other anionic species appearing in the overall formulation. In one embodiment, the anti-irritant topical formulations additionally contain an irritant ingredient(s) that is itself capable of inducing skin irritation or inflammation, as for example a cosmetic or skin care product ingredient, or a pharmaceutically active ingredient or drug ingredient.

The cations for use in the anti-irritant formulations of the invention are selected from one or more of the monovalent cations potassium ($K^+$) and lithium ($Li^+$) contained in a topical formulation in a concentration effective to prevent or reduce (hereafter, "inhibit") the skin irritation and/or inflammation that is sought to be eliminated. The formulation preferably contains the potassium cation in a suitable topical vehicle at a total concentration of about 100 to about 3000 mM, more preferably about 400 to about 2000 mM, and most preferably about 700 to about 1500 mM. In the case of the lithium cation, preferred concentrations are about 10 to about 3000 mM, more preferably about 50 to about 2000 mM, and most preferably about 100 to about 1000 mM. These preferred concentration ranges correspond to bioavailable forms of such cations within the formulation, particularly, ionizable and aqueous-soluble forms of such cations as contrasted with insoluble or covalently-bonded forms of the cations. Preliminary studies have indicated that the low-concentration anti-irritant efficacy of the lithium cation is increased if the vehicle includes glycerol, and increases may likewise be achieved with potassium cation using similar vehicle modifications.

The appropriate cation concentration can be achieved using a single metal cation species of the invention, or multiple different cation species may be combined to yield the total desired cation concentration. If other anti-irritant compounds are included in the formulation, then lower concentrations of the cations of the invention may be utilized.

Preferred cation concentrations can also be expressed in weight/volume or weight/weight percentage terms which will vary somewhat depending on the density of the vehicle and other components in the formulation. Thus, to take an example in which the vehicle has a density of 0.93 g/ml (as in a 50:50 [by volume] mixture of 95% ethyl alcohol and water) and the cation component is incorporated in the form of lithium sulfate (formula weight 110), representative molarity concentration values correspond approximately to

| | | |
|---|---|---|
| 500 mM: | 2.75% (w/v) | 2.96% (w/w) |
| 1000 mM: | 5.5% (w/v) | 5.91% (w/w) |
| 1500 mM: | 8.25% (w/v) | 8.88% (w/w) |

The preferred concentration ranges expressed above contemplate that a typical topical dosage will be approximately 0.5 grams of cation formulation over a 5 cm×5 cm area of skin (25 cm$^2$). Clinical studies have shown that such preferred concentration ranges are generally effective to inhibit skin irritation and, in typical topical vehicles, are readily formulated and do not leave any significant visible residue when applied to the skin. Higher concentration formulations, such as saturated pastes or other forms, may also be successfully used, particularly where visible appearance is not a limiting consideration (as in therapeutic applications).

Furthermore, routine clinical assessments such as those described below can readily be employed to optimize the cation concentration and to ascertain if lower, or higher, concentrations are appropriate for a given formulation or irritation indication. For example, the concentration of cation may be adjusted to account for the amount of formulation that is typically applied to a given skin area by the user, which will depend to an extent on the physical nature of the topical vehicle (e.g., lotion as compared to liquid spray vehicles). Likewise, the amount of cation required may be reduced in such cases where the formulation contains a skin penetration-enhancing ingredient or other agent which increases the ability of the cations to permeate the stratum corneum to their site of anti-irritant activity. Preferably, the formulations of the invention include an amount of anti-irritant cation (or cations) capable of inhibiting irritation in susceptible individuals by at least about 20% or more, as measured by a mean reduction in cumulative irritation across a susceptible test population as exemplified in the clinical protocols described below. Alternatively, the formulations of the invention include an amount of anti-irritant cation capable of inhibiting irritation by at least about 40% or more in at least about 10% of the susceptible population, as measured by a reduction in cumulative irritation on an individual-by-individual basis (treated vs. control areas). This latter measure of efficacy reflects the fact that the present formulations, similar to many therapeutic products, may in some cases be effective in delivering a significant benefit to some, but not all, of the susceptible population.

In one preferred embodiment, the formulations of the invention include only a single cation species of the invention (i.e., one of potassium ($K^+$) or lithium ($Li^+$) in a total concentration as described above. However, one discovery of the invention is that anti-irritant activity is generally maintained at about an "additive" level if fractional portions of different species of the cations of the invention are combined so as to make up a total combined cation concentration within the ranges referred to above. This discovery is surprising because it could not be predicted that the (fractional) anti-irritant activity attributable to a fractional portion of a given cation would be retained in the presence of another fractional portion of a different anti-irritant cation species, let alone that the respective fractional anti-irritant activities would "add" to one another as has now been observed. This result suggests that the biological modes of activity of the distinct cations of the invention are non-competitive or complementary.

The optimum concentration of a cation of the invention may also be reduced below (or within) the preferred ranges set forth above if some other anti-irritant component is included in the formulation along with the cation component of the invention. In particular, it is contemplated that lower (e.g. halved) amounts of potassium ($K^+$) or lithium ($Li^+$) cations may be used, while still maintaining comparable levels of anti-irritant activity, by further including an approximately equal concentration of, for example, a calcium-channel blocking or regulatory agent, or other anti-irritant agent such as a steroid or non-steroidal anti-inflammatory agent. Examples of suitable additional anti-irritant ingredients are described in applicants' co-pending U.S. patent application Ser. Nos. 08/362,100, 08/362,101, 08/362,097 and 08/362,058 (attorney docket numbers 209/250, 210/181, 210/182, and 210/184, entitled "Formulations and Methods for Reducing Skin Irritation"), filed Dec. 21, 1994 and incorporated by reference in their entirety. Other anti-irritant ingredients, such as aloe vera, chamomile, α-bisabolol, Cola nitida extract, green tea extract, tea tree oil, licorice extract, allantoin, urea, caffeine or other xanthines, and glycyrrhizic acid and its derivatives, may also be beneficially incorporated into the formulations of the invention in order further to inhibit irritation effects or symptoms.

The cations of the invention are typically incorporated into the present formulations by mixing an appropriate amount of a suitable salt form of the selected cation into the chosen formulation vehicle, along with such other skin care components as are desired. From a formulation standpoint, it is preferred that the selected salt be sufficiently soluble in the formulation vehicle as to allow a consistent formulation having the desired physical and topical application characteristics. It will be recognized that, depending on the formulation vehicle chosen, the salt form of the cations of the invention may dissociate within the formulation (and in this case may associate with other anions also present in the formulation), or the salt form may remain substantially associated. It is also highly preferred that the salt (or salts) chosen be sufficiently aqueous-soluble such that, upon application to the skin, the component cations (and corresponding counteranions) can dissociate and be taken up into the water-containing milieu of the skin. In addition, it will be clear that the particular salt ingredient(s) chosen should be topically acceptable and preferably will not themselves be irritating, toxic or otherwise deleterious to the user.

With these considerations in mind, it will be recognized that a variety of topically acceptable cation/counteranion salt ingredients may be utilized in the present formulations in order to achieve the objectives of the invention. Such salts can be readily identified by those skilled in the art in view of the present disclosure based on known physical (e.g., solubility), pharmacological and toxicological information and, if necessary, by the application of routine experimentation.

Examples of potentially suitable counteranion components for use with the cations of the invention include a variety of mono-, di- and trivalent inorganic and organic anions. Examples of potentially suitable inorganic anions include nitrate, sulfate, halogens (particularly F, Cl, Br and I), carbonate, bicarbonate, hydroxide, oxide, peroxide, nitrite, bisulfate, persulfate, glycerophosphate, hypophosphate, borate and titanate. Examples of potentially suitable organic anions include carboxylic acids, alkoxylates, amino acids, peptides, saturated and unsaturated organic acids, and saturated and unsaturated fatty acids. Particular examples include citrate, oxalate, acetate, gluconate, lactate, tartrate, maleate, benzoate, propionate, salicylate, ascorbate, formate, succinate, folinate, aspartate, phthalate, oleate, palmitate, stearate, lauryl sulfate, lanolate, myristate, behenate, caseinate, cyclamate, pantothenate, EDTA and other polyarninopolycarboxylates, saccharin, thioglycolate, laurate, methylparaben, propylparaben, ricinoleate and sorbate anions. It will be recognized in view of the foregoing disclosure that certain of these suitable anion components, particularly various carboxylic acid anions, are themselves known active ingredients in various topical products (e.g. exfolient products), and it will be seen accordingly that such active ingredients anions can be incorporated into useful formulations along with the anti-irritant counter-cations of the invention.

Clinical trials relating to the invention have established that certain cation-anion pairs are particularly active as anti-irritants. These include potassium nitrate, potassium chloride, potassium oxalate, and potassium gluconate; and lithium acetate, lithium carbonate, lithium sulfate and lithium nitrate.

Also preferred are these and other cation-anion pairs in which the anionic species is acidic, because such pairs will generally exhibit higher solubility in many common topical vehicles and suitable ionization upon application to the skin. In addition, strongly acidic anion components may be useful where it is desired to maintain the pH of the resulting formulation at a relatively acidic level, as for example in the case of hydroxy-acid or other acidic exfolient products where the activity of the product to reduce wrinkles or bring about other beneficial effects may be reduced if the formulation is not relatively acidic. In any event, however, the desired level of acidity in such cases can be achieved by adjusting the formulation with a suitable acid (or base if necessary).

In one such particularly preferred embodiment, a cation of the present invention is combined in a hydroxy acid or other exfolient preparation accompanied by one or more suitable anionic or other acidic species such that the pH of the hydroxy acid preparation is maintained in the range of pH 1–6, and more preferably in the range of pH 3–5. It will be understood that, where the formulation employs an anhydrous vehicle, the acidity of the formulation may not be expressible in typical pH terms, but that such acidity will manifest itself upon exposure of the formulation to the skin where water is present both intracellularly and extracellularly.

Suitable topical vehicles for use with the formulations of the invention are well known in the cosmetic and pharmaceutical arts, and include such vehicles (or vehicle components) as water; organic solvents such as alcohols (particularly lower alcohols readily capable of evaporating from the skin such as ethanol), glycols (such as glycerin), aliphatic alcohols (such as lanolin); mixtures of water and organic solvents (such as water and alcohol), and mixtures of organic solvents such as alcohol and glycerin (optionally also with water); lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile) such as cyclomethicone, demethiconol and dimethicone copolyol (Dow Coming); hydrocarbon-based materials such as petrolatum and squalane; anionic, cationic and amphoteric surfactants and soaps; sustained-release vehicles such as microsponges and polymer matrices; stabilizing and suspending agents; emulsifying agents; and other vehicles and vehicle components that are suitable for administration to the skin, as well as mixtures of topical vehicle components as identified above or otherwise known to the art. The vehicle may further include components adapted to improve the stability or effectiveness of the applied formulation, such as preservatives, antioxidants, skin penetration enhancers, sustained release materials, and the like. Examples of such vehicles and vehicle components are well known in the art and are described in such reference works as *Martindale—The Extra Pharmacopoeia* (Pharmaceutical Press, London 1993) and Martin (ed.), *Remington's Pharmaceutical Sciences*.

The choice of a suitable vehicle will depend on the particular physical form and mode of delivery that the formulation is to achieve. Examples of suitable forms include liquids (including dissolved forms of the cations of the invention as well as suspensions, emulsions and the like); solids and semisolids such as gels, foams, pastes, creams, ointments, "sticks" (as in lipsticks or underarm deodorant sticks), powders and the like; formulations containing liposomes or other delivery vesicles; rectal or vaginal suppositories, creams, foams, gels, ointments, enemas, douches and other forms. Typical modes of delivery include application using the fingers; application using a a physical applicator such as a cloth, tissue, swab, stick or brush (as achieved for example by soaking the applicator with the formulation just prior to application, or by applying or adhering a prepared applicator already containing the formulation—such as a treated or premoistened bandage, wipe, washcloth or stick—to the skin); spraying (including mist, aerosol or foam spraying); dropper application (as for example with ear drops); sprinkling (as with a suitable powder form of the formulation); and soaking.

Methodologies and materials for preparing formulations in a variety of forms are also described in Anthony L. L. Hunting (ed.), "A Formulary of Cosmetic Preparations (Vol. 2)—Creams, Lotions and Milks," Micelle Press (England, N.J. 1993). See, for example, Chapter 7, pp. 5–14 (oils and gels); Chapter 8, pp. 15–98 (bases and emulsions); Chapter 9, pp. 101–120 ("all-purpose products"); Chapter 10, pp. 121–184 (cleansing masks, creams, lotions); Chapter 11, pp. 185–208 (foundation, vanishing and day creams); Chapter 12, pp. 209–254 (emollients); Chapter 13, pp. 297–324 (facial treatment products); Chapter 14, pp. 325–380 (hand products); Chapter 15, pp. 381–460 (body and skin creams and lotions); and Chapter 16, pp. 461–484 (baby products); the contents of which are incorporated herein by reference.

The formulations of the invention are most preferably formulated such that the cation component of the formulation (as occurring with any accompanying anion counterion components) is substantially invisible upon application to the skin. This is particularly true in the case of many cosmetic formulations that are applied to the face or other exposed parts of the body, although it is also generally desirable that the cation (and anion) component not be visible even if applied to non-exposed portions of the body. It will be recognized that in some cases, particularly with colored facial skin care products such as blushes, blemish covers, lipsticks and the like, the formulation will be designed to be visible on the skin; in such cases, it is desirable that the cation component itself be "invisible," that is, that it not adversely change the appearance of the overall formulation as applied to the skin.

In another embodiment of the invention, the present cations can be be formulated in a form for topical oral administration to treat pain or irritation in the mouth or throat such as that due to sore throats, canker sores, gum irritation or inflammation or the like, including such irritation as may be exacerbated by spicy or acidic foods. Furthermore, it is believed that the present cations (and their suitable oral salts) are generally tasteless at the concentrations described. Suitable forms for such oral administration include liquids (e.g. mouthwash or gargle solutions) and lozenges. As with other topical forms described herein, the components used in such oral formulations (including the cation salts) should be chosen to be non-toxic. Methods for preparing oral formulations suitable for use in the present invention are well known in the art.

Clinical Results

The anti-irritant efficacy of the formulations of the present invention was tested and confirmed in numerous clinical trials, the results of which are described in the examples below. While these examples further illustrate various aspects and preferred embodiments of the invention as described herein, they are examples only, and should not be considered as limiting the scope of the invention as set forth in the claims.

EXAMPLE 1

Clinical Studies of Anti-Irritation Activity

The objective of the clinical trials was to determine whether and to what extent the cations of the present invention reduced or prevented skin irritation caused by lactic acid, an α-hydroxy carboxylic acid known for its skin irritating potential. The trials were conducted in a double blind, randomized, vehicle-controlled manner. Various formulations of the invention were tested in over 550 people. The results confirm the highly reproducible anti-irritant activity of the cations and formulations of the present invention.

1. Protocol

The subjects were women who had been screened and shown to exhibit normal to above normal susceptibility to irritation by the tested irritant. Tests were conducted in multiple panels of from 7 to 12 subjects each. Subjects were instructed not to wear any makeup or facial lotions to the clinic the day of testing. The subjects were instructed to wash their face with Ivory bar soap in the clinic prior to application of test solutions.

Lactic acid skin-irritant compositions were formulated in an appropriate vehicle prior to application to the skin of the subjects. In the majority of the tests, the irritant composition was 7.5% lactic acid dissolved in a 10% ethanol-in-water solution.

Test anti-irritant formulations were prepared by combining measured amounts of salts of the cations of the present invention (concentration 250 mM) in the lactic acid irritant composition. The test formulation was applied to a defined portion of the subject's skin, typically the face. Controls were performed by applying a corresponding formulation without any added cation to a contralateral portion of the subject's skin.

All test solutions (including controls) were applied in a double blind, randomized fashion using the prepared solutions as previously placed in coded vial designated for use on either the right or left side of the face (or other test area). Solutions were typically applied using a cotton swab (six strokes) or sponge applicator to the face and cheek area extending from the midline of the nose over to the center of the cheek and from the cheek bone down to the jaw line. Application was made first to the right side and then to the left.

Sensory assessment scores were recorded for each treated side of the subject's skin every minute for 15 minutes or until three consecutive scores of "zero" irritation were obtained. The following scaled scores were used for sensory assessment:

| Score | Description of Irritation |
|---|---|
| 0 | NO irritation |
| 1 | SLIGHT irritation - (Barely perceptible stinging, burning or itching) |
| 2 | MILD irritation - (Definite stinging, burning or itching) |
| 3 | MODERATE irritation - (Distinctly uncomfortable stinging, burning or itching; constantly aware of irritation) |
| 4 | SEVERE irritation - (Continuous stinging, burning or itching, and intensely uncomfortable; would interfere with daily routine) |

Symptom scores were cumulated, separately for the cation-treated and control-treated areas, for each individual and also for the panel as a whole. Individuals not reporting a cumulative score of at least "7" on at least one treatment area were excluded (in a blinded fashion) from further analysis in order to ascertain anti-irritant efficacy with respect to the more severely-susceptible test subjects. From a practical standpoint, scores of "0" and "1" on the above scale would be considered highly desirable for a commercial product because such a response would likely not result in a consumer ceasing to use a product. Some consumers, in fact, might view the "barely perceptible" sensations represented by a score of 1 to be an indication that a facial treatment skin care product (especially an exfoliant) was working as advertised. By contrast, irritation scores of "2", "3" and "4" would likely often result in a consumer never purchasing the product again.

In those subjects and skin samples where an irritation was sensed, the irritation commonly involved a spectrum of burn-sting-itch reactions over time. For example, a subject might at first experience a sting, but moments later might experience an itch with no sting. Subjects experiencing higher levels of irritation (e.g. scores of "3" or "4") occasionally exhibited erythema (visually observable inflammation) in addition to sensory irritation effects.

2. Results

Clinical tests of over 550 subjects, performed as generally described above, demonstrated that the cations of the invention have significant and reproducible anti-irritant effects, particularly if administered simultaneously with an irritant compound. The average inhibition of cumulative irritation for various cation salts of the invention at 250 mM are shown in the following table.

| Cation Salt | Percent Inhibition |
|---|---|
| Potassium chloride | 40% |
| Potassium nitrate | 30% |
| Potassium sulfate | 15% |
| Potassium gluconate | 25% |
| Lithium chloride | 0% |
| Lithium nitrate | 20% |
| Lithium sulfate | 35% |
| Lithium acetate | 70% |

A representative set of test results from several subject panels, performed using cation concentrations of 250 mM, is set forth in the following tables.

ANTI-IRRITANT CATION DATA

| Cation | Anion | Salt Formula | Vehicle | Percent Inhibition |
|---|---|---|---|---|
| Potassium | Chloride | KCl | 10% EtOH | 38 |
| Potassium | Nitrate | $KNO_3$ | 10% EtOH | 29 |
| Potassium | Sulfate | $K_2SO_4$ | 10% EtOH | 27 |
| Potassium | Gluconate | $K[CH_2OH(CHOH)_4CO_2]$ | 10% EtOH | 25 |
| Potassium | Oxalate | $K_2(CO_2)_2$ | 10% EtOH | 30 |
| Lithium | Chloride | LiCl | 10% EtOH | 6 |
| Lithium | Nitrate | $LiNO_3$ | 10% EtOH | 16 |
| Lithium | Sulfate | $Li_2SO_4$ | 10% EtOH | 39 |
| Lithium | Acetate | $Li(CH_3CO_2)$ | 10% EtOH | 67 |
| Lithium | Carbonate | $Li_2CO_3$ | 10% EtOH | 69 |

Figure 2:
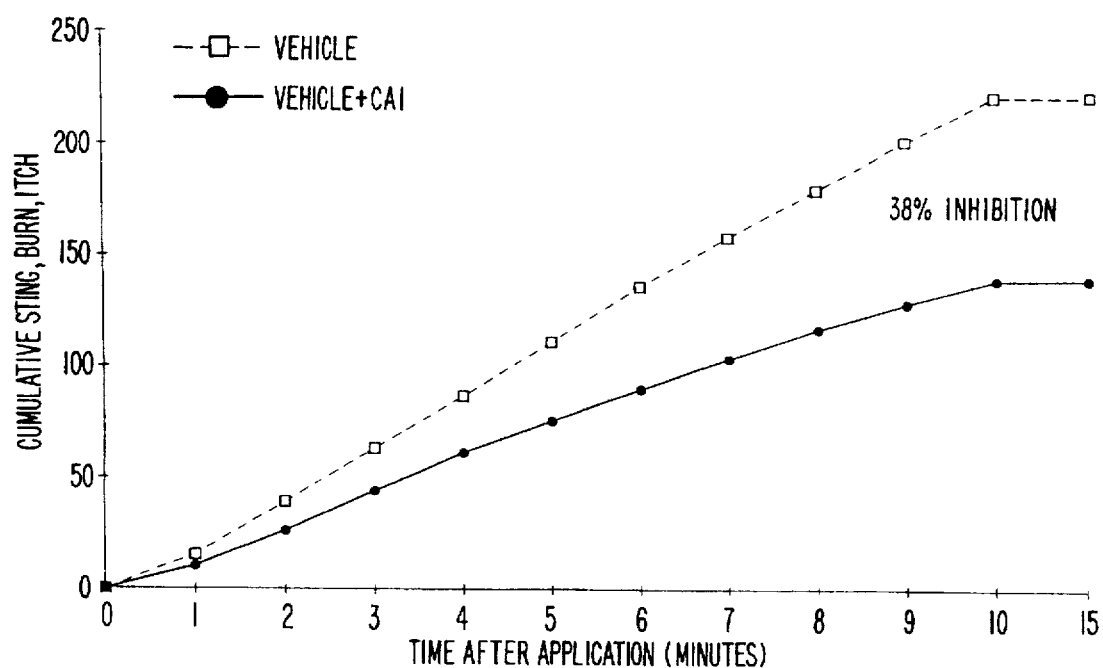
Figure 3:
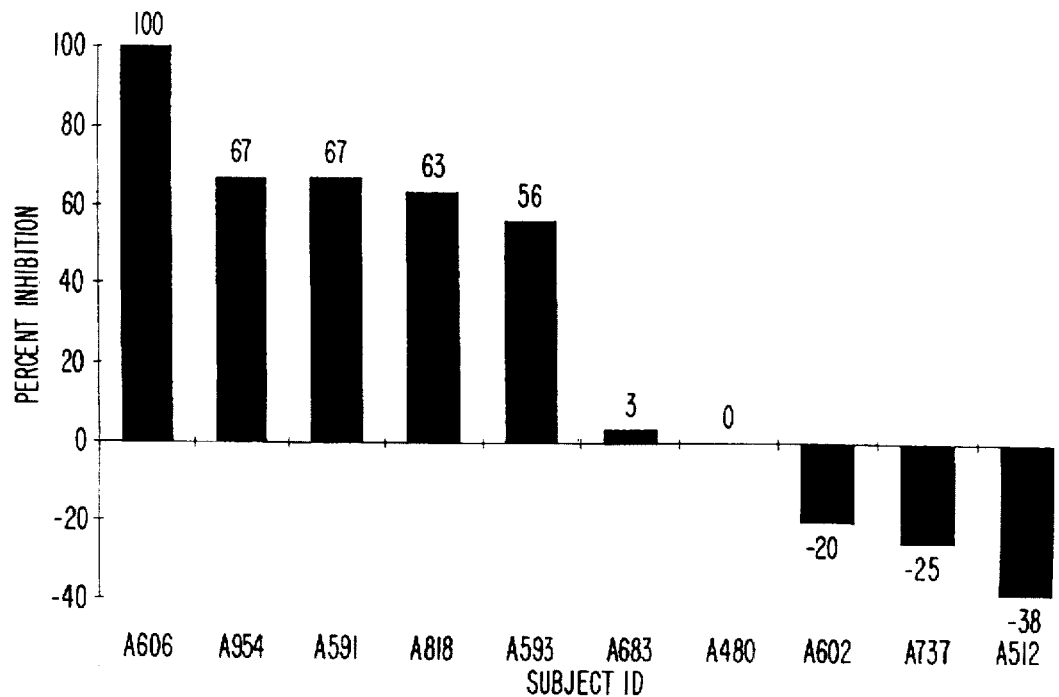
Figure 4:
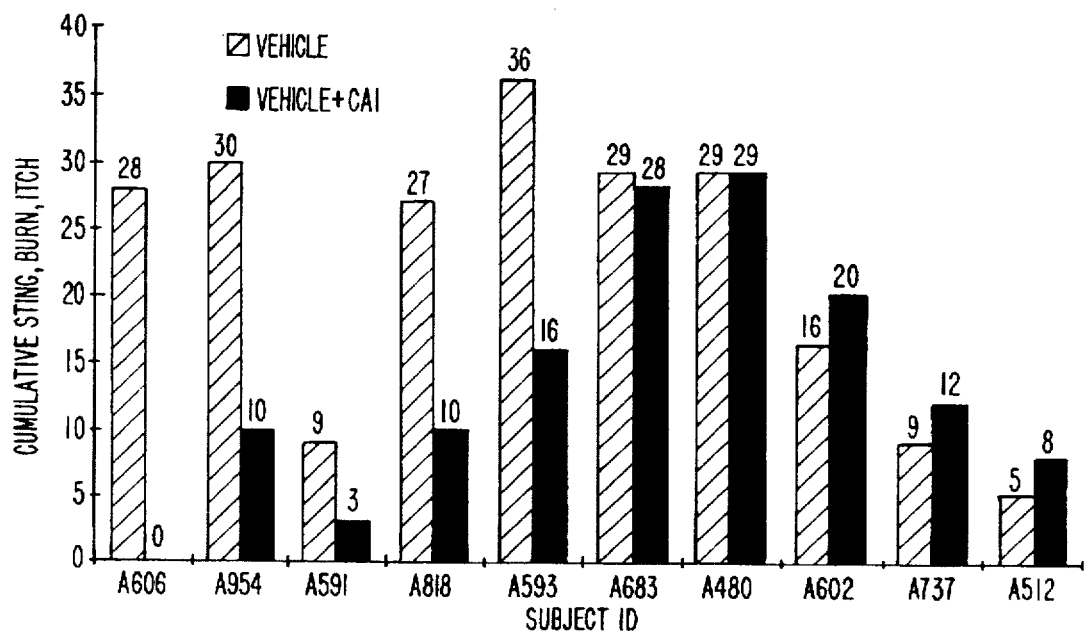
Figure 5:
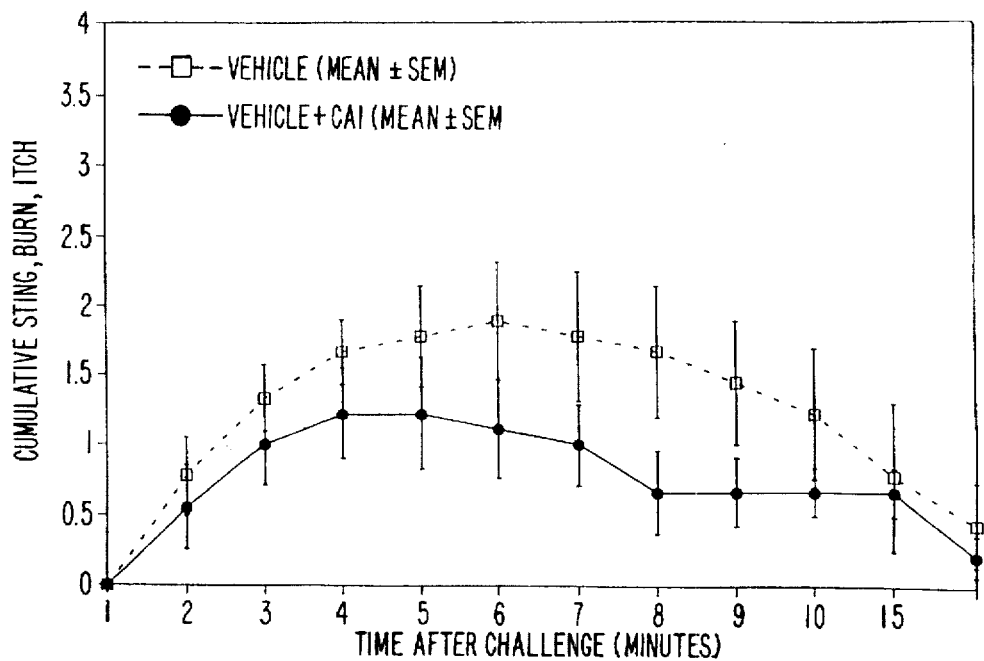
FIGS. 5 through 8 depict experimental data showing the time course of irritation responses (FIG. 5), the cumulative irritation over time (FIG. 6), and the subject-by-subject cumulative irritation suppression and irritation responses (FIGS. 7 and 8) for a panel of humans treated with 250 mM lithium sulfate (and control) in a lactic acid skin irritation challenge.
Figure 6:
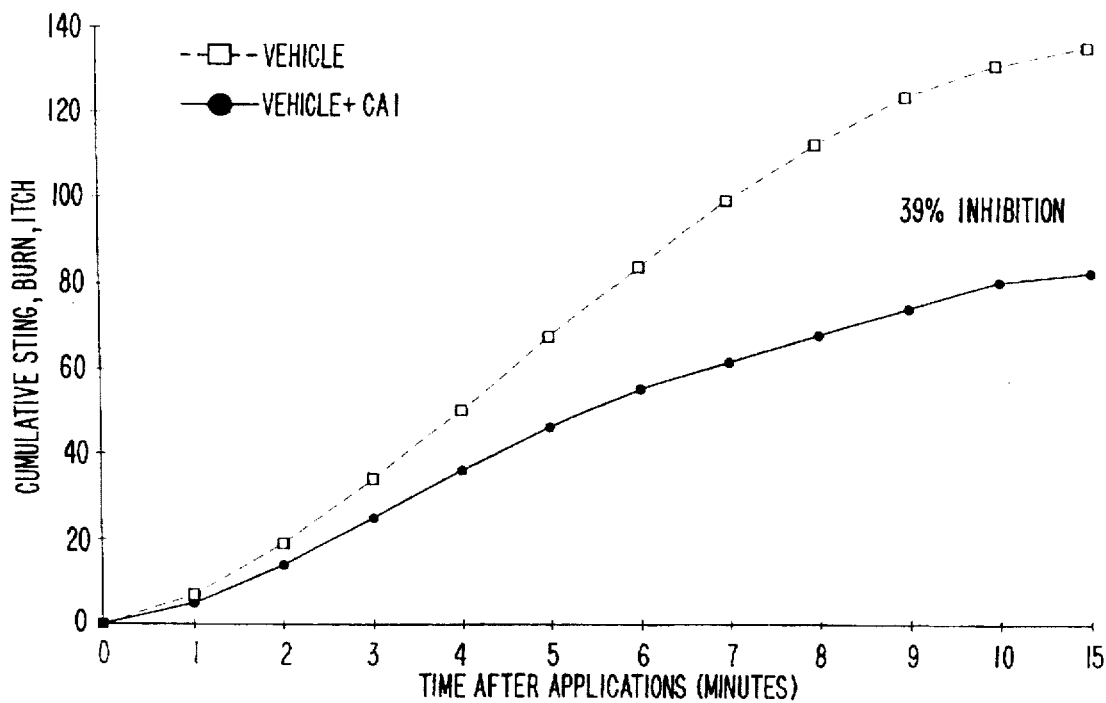
Figure 7:
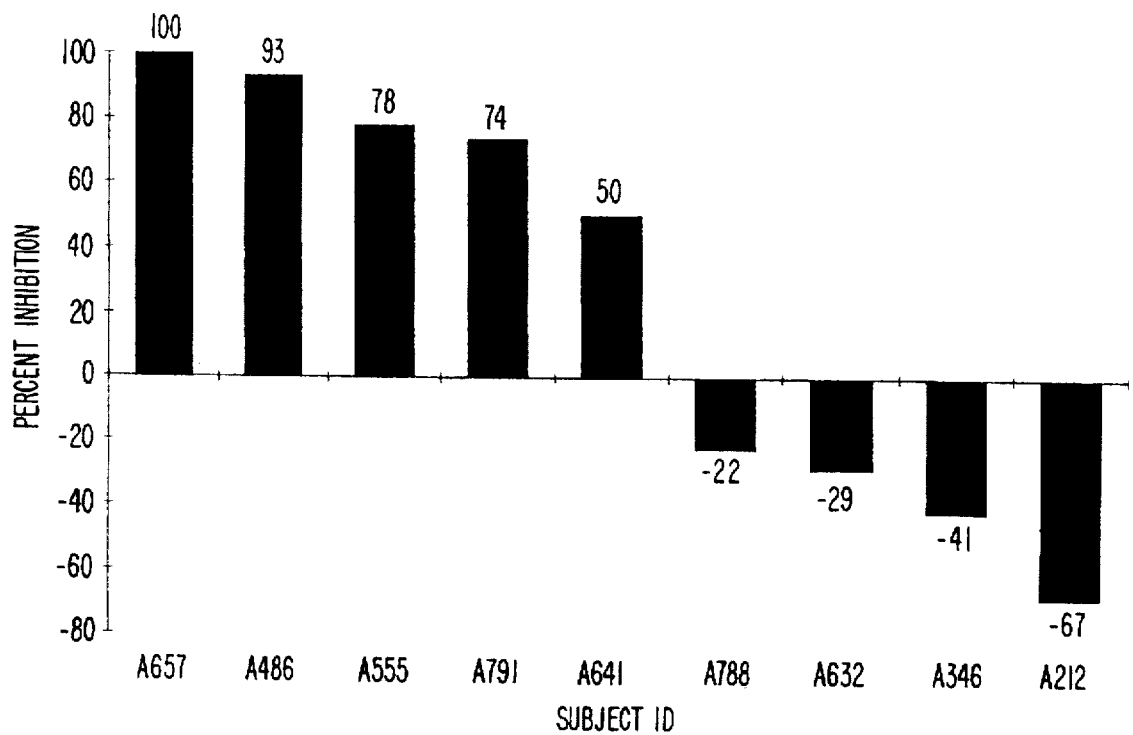
Figure 8:
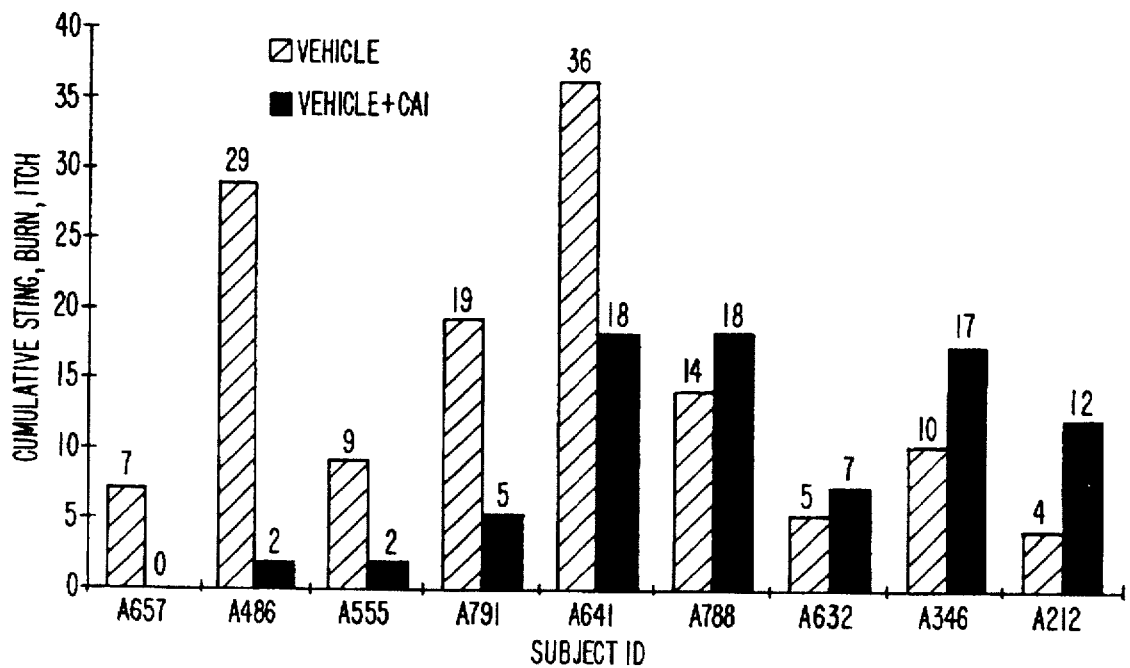

FIGS. 1 through 8 show more detailed experimental data for two panel tests conducted using lithium sulfate and potassium chloride (250 mM each) as anti-irritant salt components of the subject formulations. FIGS. 1 and 5 show the time course of irritation responses for both cation-treated and non-treated (control) skin portions for the panels. FIGS. 2 and 6 show the cumulative irritation over time for the same panels, while FIGS. 3–4 and 7–8 show cumulative irritation suppression and treated/untreated irritation responses on a subject-by-subject basis. While individual responses vary somewhat, the overall efficacy of the subject formulations is evident.

EXAMPLE 2

Dose-Response Studies

Figure 9:
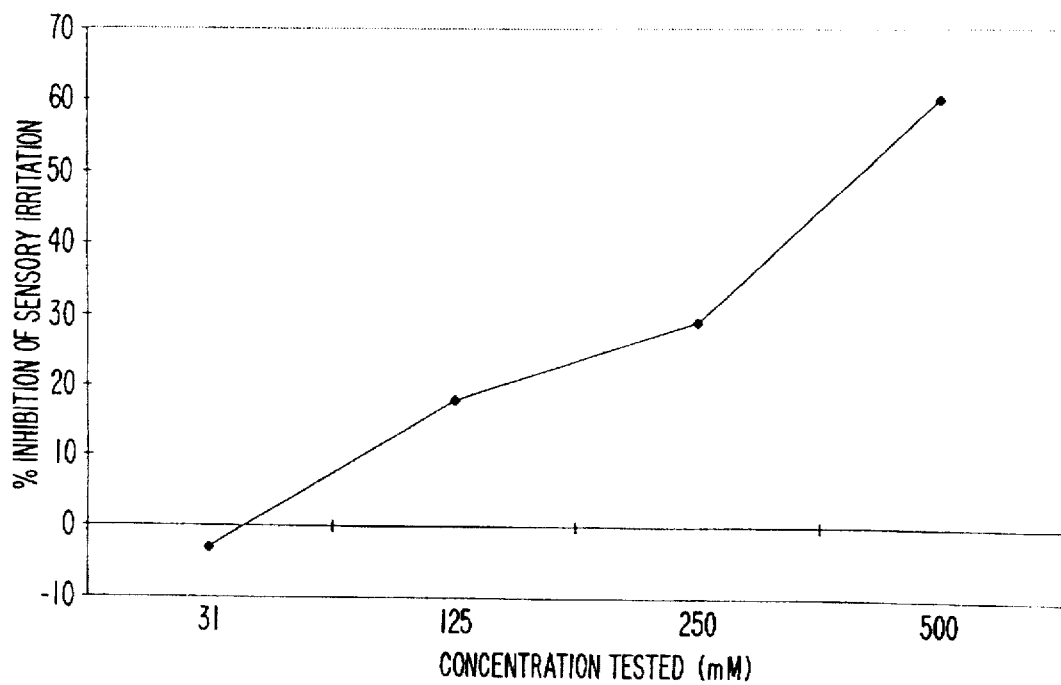
FIG. 9 depicts experimental data showing the cumulative irritation inhibition effects of potassium nitrate administered at varying concentrations (31–500 mM) in a lactic acid skin irritation challenge.
Figure 10:
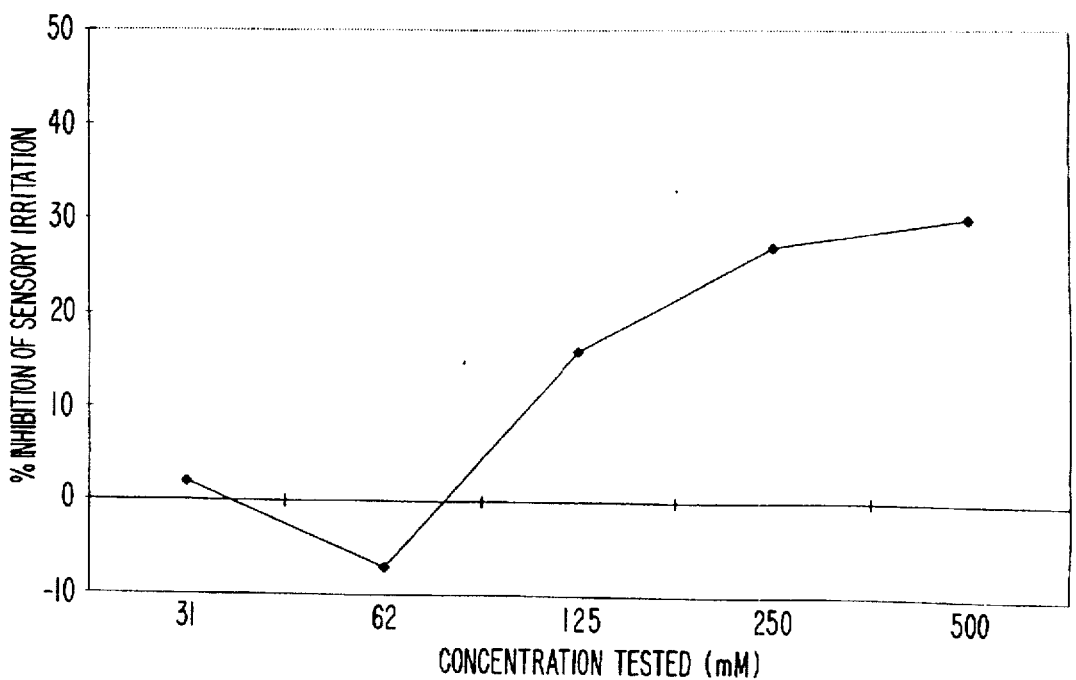
FIG. 10 depicts experimental data showing the cumulative irritation inhibition effects of lithium sulfate administered at varying concentrations (31–500 mM) in a lactic acid skin irritation challenge.

Additional studies of anti-irritant activity using varying concentrations of potassium and lithium cations were conducted in order to assess the dose-response behavior of the present formulations. The lactic acid protocol described above was used, in which the anti-irritant cation components were potassium nitrate or lithium sulfate (31–500 mM). Cumulative irritation data are set forth in the following tables, and are depicted in FIGS. 9 and 10.

| | Percent Inhibition |
|---|---|
| Potassium Nitrate Concentration (mM) | |
| 31 | −3 |
| 125 | 18 |
| 250 | 29 |
| 500 | 60 |
| Lithium Sulfate Concentration (mM) | |
| 31 | 2 |
| 62 | −7 |
| 125 | 16 |
| 250 | 27 |
| 500 | 30 |

EXAMPLE 3

Additional Formulation Examples

Cation salts of the invention were formulated at various concentrations in various commercially available topical cosmetic products. The resulting mixtures generally did not alter the texture, color, consistency or other physical properties of the product, and could be used as formulations to inhibit topical irritation.

Topical solution forms of potassium nitrate, potassium chloride, potassium citrate, lithium sulfate, lithium nitrate and lithium acetate were prepared by combining various amounts of the named salts with Elizabeth Arden Visible Difference Refining Toner (an alcohol-containing solution). The concentrations achieved were shown to be effective to inhibit skin irritation.

The foregoing examples are not intended to limit the scope of the present invention, which is set forth in the following claims. In particular, various equivalents and substitutions will be recognized by those skilled in the art in view of the foregoing disclosure, and these are contemplated to be within the scope of the invention.

What is claimed is:

1. A composition for topical application to an animal subject comprising
a topical vehicle;
an irritant ingredient selected from the group consisting of carboxylic acids, keto acids, α-hydroxy acids, β-hydroxy acids, retinoids, peroxides, organic alcohols, and mixtures thereof said irritant ingredient being contained in an amount capable of inducing skin irritation in said subject; and an anti-irritant metal cation consisting essentially of aqueous-soluble monovalent lithium cation, said anti-irritant metal cation being contained in a concentration of at least about 100 mM and capable of inhibiting mean cumulative skin irritation attributable to said irritant ingredient in the human population susceptible to said skin irritation by at least about 20%.

2. The composition of claim 1 comprising lithium cation in a concentration of from about 100 mM to about 3000 mM.

3. The composition of claim 1 comprising lithium cation in a concentration of from about 100 mM to about 2000 mM.

4. The composition of claim 1 comprising lithium cation in a concentration of from about 100 mM to about 1000 mM.

5. The composition of claim 1 wherein said inhibition of skin irritation represents an average reduction in one or more of sting, burn and itch in the human population susceptible to said skin irritation upon topical application of said composition, as compared to the level of irritation induced in said population upon topical application of a control formulation containing said irritant ingredient in a vehicle without said cation.

6. The composition of claim 1 comprising an amount of lithium cation capable of inhibiting by at least about 40% the cumulative skin irritation attributable to said irritant ingredient in at least 10% of the human population susceptible to said skin irritation.

7. The composition of claim 6 wherein said inhibition of skin irritation represents an average reduction in one or more of sting, burn and itch in at least 10% of the human population susceptible to said skin irritation upon topical application of said composition, as compared to the level of irritation induced in said at least 10% of the population upon topical application of a control formulation containing said irritant ingredient in a vehicle without said cation.

8. The composition of claim 1 wherein said composition is a cosmetic product.

9. The composition of claim 8 wherein said composition comprises a skin exfolient, skin peel or skin cell renewal agent.

10. The composition of claim 1 wherein said irritant ingredient comprises lactic acid or a salt thereof.

11. The composition of claim 1 wherein said irritant ingredient comprises glycolic acid or a salt thereof.

12. The composition of claim 1 wherein said irritant ingredient comprises salicylic acid or a salt thereof.

13. The composition of claim 1 wherein said irritant ingredient comprises a combination of lactic acid and salicylic acid, or salts thereof.

14. The composition of claim 1 wherein said irritant ingredient comprises capryloyl salicylic acid or a salt thereof.

15. The composition of claim 1 wherein said irritant ingredient comprises citric acid or a salt thereof.

16. The composition of claim 1 wherein said irritant ingredient is a retinoid selected from tretinoin, retinol, and retinal.

17. The composition of claim 1 wherein said irritant ingredient comprises benzoyl peroxide.

18. The composition of claim 1 wherein said irritant ingredient comprises acetic acid or a salt thereof.

19. The composition of claim 1 wherein said irritant ingredient comprises an ingredient selected from the group consisting of 1-pyrrolidone-5-carboxylic acid, capryloyl salicylic acid, α-hydroxy decanoic acid, α-hydroxy octanoic acid, gluconolactone, methoxypropyl gluconamide, oxalic acid, malic acid, tartaric acid, mandelic acid, benzylic acid, gluconic acid, pyruvic acid and phenol.

20. The composition of claim 1 wherein said irritant ingredient comprises trichloroacetic acid of a salt thereof.

21. The composition of claim 1 wherein the pH of the composition is in the range of 1 to 6.

22. The composition of claim 1 wherein the pH of the composition is in the range of 3 to 5.

23. The composition of claim 1 having a concentration of said irritant ingredient of from about 0.1% to about 50%.

24. The composition of claim 1 having a concentration of said irritant ingredient of from about 0.5% to about 20%.

25. The composition of claim 1 wherein said composition is an antiperspirant or deodorant product.

26. The composition of claim 1 wherein said composition is a sunscreen, tanning or sunburn treatment product.

27. The composition of claim 1 wherein said composition is an insect repellant product.

28. The composition of claim 8 wherein said composition is a shaving or hair removal product selected from the group consisting of depilatory, bracer, cream, foam, gel and aftershave products.

29. The composition of claim 8 wherein said composition is a hair care or hair treatment product.

30. The composition of claim 29 wherein said composition is selected from the group consisting of shampoo, conditioner, colorant, dye, bleach, permanent wave and hair straightener products.

31. The composition of claim 8 wherein said composition is selected from the group consisting of cleansers, astringents, toners, rinses, serums and masks.

32. The composition of claim 8 wherein said composition is a facial cosmetic product.

33. The composition of claim 8 wherein said composition is selected from the group consisting of creams, lotions and moisturizers.

34. The composition of claim 1 wherein said composition is selected from the group consisting of soaps and detergents.

35. The composition of claim 1 wherein said composition is a topical drug product.

36. The composition of claim 35 wherein said irritant ingredient is capsaicin.

37. The composition of claim 35 wherein said composition is selected from the group consisting of antibiotic, analgesic, contraceptive, anti-acne and anti-dandruff products.

38. The composition of claim 37 wherein said irritant ingredient is benzoyl peroxide.

39. The composition of claim 1 wherein said composition is formulated as a rectal or vaginal suppository, foam, cream, gel, ointment, douche or enema.

40. The composition of claim 1 wherein said composition is formulated for administration to the mouth, throat or lip.

41. The composition of claim 40 formulated as a lozenge, mouthwash or gargle.

42. The composition of claim 1 formulated as a liquid, gel, cream, emulsion, suspension or stick.

43. The composition of claim 1 formulated with a physical applicator.

44. The composition of claim 43 wherein said physical applicator is selected from the group consisting of cloths, tissues, swabs, bandages and wet wipes.

45. The composition of claim 1 further comprising, as counteranions to said cation, one or more topically acceptable anion species.

46. The composition of claim 1 further comprising, as counteranions to said cation, one or more anion species selected from the group consisting of nitrate, sulfate, halogen, carbonate, bicarbonate, hydroxide, oxide, peroxide, nitrite, bisulfate, persulfate, glycerophosphate, hypophosphate, borate and titanate inorganic anions, and carboxylic acid, alkoxylate, amino acid, peptide, saturated and unsaturated organic acid, and saturated and unsaturated fatty acid organic anions.

47. The composition of claim 46 wherein said one or more of said counteranions is an organic anion selected from the group consisting of citrate, oxalate, acetate, gluconate, lactate, tartrate, maleate, benzoate, propionate, salicylate, ascorbate, formate, succinate, folinate, aspartate, phthalate, oleate, palmitate, stearate, lauryl sulfate, lanolate, myristate, behenate, caseinate, cyclamate, pantothenate, polyaminopolycarboxylates, saccharin, thioglycolate, laurate, methylparaben, propylparaben, ricinoleate and sorbate organic anions.

48. The composition of claim 45 wherein said anion species includes nitrate.

49. The composition of claim 45 wherein said anion species includes sulfate.

50. The composition of claim 45 wherein said anion species includes a halogen selected from chloride and fluoride anions.

51. The composition of claim 1 further comprising at least one second anti-irritant agent.

52. The composition of claim 51 wherein the total amount of said lithium cation and said second agent is capable of inhibiting by at least about 40% the cumulative skin irritation attributable to said irritant ingredient in at least 10% of the human population susceptible to said skin irritation.

53. The composition of claim 51 wherein said second agent is selected from the group consisting of potassium channel mediating, regulating or blocking agents, calcium channel blocking or regulatory agents, sodium channel blocking agents, steroids, non-steroidal anti-inflammatory agents, aloe vera, chamomile, α-bisabolol, Cola nitida extract, green tea extract, tea tree oil, licorice extract, allantoin, urea, caffeine and other xanthines, and glycyrrhizic acid.

54. A method of inhibiting skin irritation associated with an irritant ingredient contained in an applied topical formulation, said irritant ingredient being selected from the group consisting of carboxylic acids, keto acids, α-hydroxy acids, β-hydroxy acids, retinoids, peroxides, organic alcohols, and mixtures thereof comprising topically administering to an animal subject a composition comprising a topical vehicle;

said irritant ingredient contained in an amount capable of inducing skin irritation in said subject; and an anti-irritant amount of aqueous-soluble monovalent lithium cation, said lithium cation being contained in a concentration of at least about 100 mM.

* * * * *